(12) United States Patent
Keck

(10) Patent No.: US 9,040,105 B2
(45) Date of Patent: May 26, 2015

(54) NANOCRYSTALS AND AMORPHOUS NANOPARTICLES AND METHOD FOR PRODUCTION OF THE SAME BY A LOW ENERGY PROCESS

(71) Applicant: PharmaSol GmbH, Berlin (DE)

(72) Inventor: Cornelia Keck, Schwielowsee (DE)

(73) Assignee: PHARMASOL GMBH, Berlin (DE)

( * ) Notice: Subject to any disclaimer, the term of this patent is extended or adjusted under 35 U.S.C. 154(b) by 0 days.

(21) Appl. No.: 13/649,470

(22) Filed: Oct. 11, 2012

(65) Prior Publication Data

US 2013/0095198 A1 Apr. 18, 2013

(30) Foreign Application Priority Data

Oct. 17, 2011 (EP) ..................................... 11185527

(51) Int. Cl.
*A61K 36/87* (2006.01)
*A61K 9/14* (2006.01)
*A61K 9/00* (2006.01)

(52) U.S. Cl.
CPC ............... *A61K 9/145* (2013.01); *A61K 9/0095* (2013.01); *A61K 36/87* (2013.01); *Y10S 977/773* (2013.01); *Y10S 977/90* (2013.01)

(58) Field of Classification Search
None
See application file for complete search history.

(56) References Cited

U.S. PATENT DOCUMENTS

| | | | |
|---|---|---|---|
| 2,789,800 A | 4/1957 | Willems | |
| 5,858,410 A | 1/1999 | Muller | |
| 6,337,092 B1 | 1/2002 | Khan | |
| 6,494,924 B1 | 12/2002 | Auweter | |
| 2006/0024248 A1* | 2/2006 | Spengler et al. | 424/49 |
| 2008/0279928 A1* | 11/2008 | Moschwitzer | 424/455 |
| 2010/0047297 A1* | 2/2010 | Petersen | 424/401 |

FOREIGN PATENT DOCUMENTS

| | | |
|---|---|---|
| DE | 10 2005 011 786 | 9/2006 |
| DE | 10 2005 017 777 | 10/2006 |
| GB | 2200048 | 2/1991 |
| WO | 96/14830 A1 | 5/1996 |
| WO | 01/03670 A1 | 1/2001 |
| WO | 2006/094808 A2 | 9/2006 |
| WO | 2006/108637 A2 | 10/2006 |
| WO | 2008/058755 A1 | 5/2008 |
| WO | 2008/065506 A2 | 6/2008 |

OTHER PUBLICATIONS

Badescu et al, On encapsulating and delivery of polyphenols in superparamagnetic polymer nanospheres. Studii si Cercetari Stiintifice: Chimie si Inginerie Chimica, Biotehnologii, Industrie Alimentara (Universitatea Bacau) (2008), 9(2), 221-228.*
Shegokar et al, Production & stability of stavudine solid lipid nanoparticles—from lab to industrial scale. International journal of pharmaceutics, (Sep. 20, 2011) vol. 416, No. 2, pp. 461-70.*
Kamiya et al, Scale-up factor for mean drop diameter in batch rotor-stator mixers. Journal of Chemical Engineering of Japan (2010), 43(4-7), 326-332.*
Mattivi, F, Vrhovsek, U, Masuero, D, Trainotti, D, Differences in the amount and structure of extractable skin and seed tannins amongst red grape varieties; Australian Journal of Grape and Wine Research 2009; 15: 27-35.
Bertelli, AA, Gozzini, A, Stradi, R, Stella, S, Bertelli, A; Stability of resveratrol over time and in the various stages of grape transformation. Drugs Exp Clin Res 1998; 24: 207-11.
Müller, R.H., C.M. Keck, Challenges and solutions for the delivery of biotech drugs—a review of drug nanocrystal technology and lipid nanoparticles. J Biotechnol, 2004. 113(1-3): p. 151-70.
Keck, CM, Müller, RH, Drug nanocrystals of poorly soluble drugs produced by high pressure homogenisation. Eur J Pharm Biopharm 2006; 62: 3-16.
Müller, RH, Gohla, S, Keck, CM, State of the art of nanocrystals—special features, production, nanotoxicology aspects and intracellular delivery. Eur J Pharm Biopharm 2011; 78: 1-9.
Keck, C, Kobierski, S, Mauludin, R, Müller, RH, Second generation of drug nanocrystals for delivery of poorly soluble drugs: smartCrystals technology, Dosis 2, 126-130, 2008.
Möschwitzer, J, Müller RH, Spray coated pellets as carrier system for mucoadhesive drug nanocrystals. Eur J Pharm Biopharm 2006; 62: 282-7.
Mishra, PR, Al Shaal L, Müller RH, Keck CM, Production and characterization of Hesperetin nanosuspensions for dermal delivery. Int J Pharm 2009; 371: 182-9.
Mauludin, R, Müller RH, Keck CM, Kinetic solubility and dissolution velocity of rutin nanocrystals. Eur J Pharm Sci 2009; 36: 502-10.
Mauludin, R, Müller RH, Keck CM, Development of an oral rutin nanocrystal formulation. Int J Pharm 2009; 370: 202-9.
Kobierski, S, Ofori-Kwakye K, Müller RH, Keck CM, Resveratrol nanosuspensions for dermal application—production, characterization, and physical stability. Pharmazie 2009; 64: 741-7.
Kobierski, S, Hanisch, J, Mauludin, R, Müller, RH, Keck, C, Nanocrystal production by smartCrystal combination technology, Int. Symp Control Rel Bioact Mater 35, #3239, New York City, 2008.
European Search Report issued in European Patent Application No. 11185527.6-1219, Feb. 24, 2012, pp. 1-8.

* cited by examiner

*Primary Examiner* — Qiuwen Mi

(74) *Attorney, Agent, or Firm* — Jeffrey S. Melcher; Manelli Selter PLLC

(57) ABSTRACT

A process for the production of nanocrystals or amorphous nanoparticles of actives (nanomaterials), especially from the peels of grapes. A dispersion of a micrometer-sized material in a solution of surfactant or a steric stabilizer is first provided. The macrosuspension is then stirred for at least 1 minute at a rotational speed above 500 rpm using a rotor-stator mixer. The stirred mixture is passed through a jet stream or piston-gas type high pressure homogenizer. The nanomaterials produced can be incorporated into formulations for use as nutraceutical, nutritional supplement, or as supportive treatment in medical therapy. The active can be derived from the peels of grapes.

22 Claims, 2 Drawing Sheets

NANOCRYSTALS AND AMORPHOUS NANOPARTICLES AND METHOD FOR PRODUCTION OF THE SAME BY A LOW ENERGY PROCESS

This application claims foreign priority to European Patent Application No. 11185527.6, filed 17 Oct. 2011, the complete disclosure of which is incorporated herein by reference.

FIELD OF THE INVENTION

The invention relates to a process to produce nanocrystals or amorphous nanoparticles of actives (nanomaterials), especially derived from the peels of grapes. Moreover, the invention relates to nanomaterials as produced by said process, and formulations comprising the same.

BACKGROUND OF THE INVENTION

Many plant materials are antioxidative, but have limited effect in vivo because of their poor solubility and low dissolution velocity. Examples are the antioxidants rutin and resveratrol (see Mattivi, F, Vrhovsek, U, Masuero, D, Trainotti, D, Differences in the amount and structure of extractable skin and seed tannins amongst red grape varieties; Australian Journal of Grape and Wine Research 2009; 15: 27-35; Bertelli, A A, Gozzini, A, Stradi, R, Stella, S, Bertelli, A; Stability of resveratrol over time and in the various stages of grape transformation. Drugs Exp Clin Res 1998; 24: 207-11), obtained from plants and being present in food and drinks (e.g. resveratrol in red wines). Therefore, they are not suitable for effective products, e.g. nutraceuticals or as drug in supportive cancer therapy. However it is described in the literature that nanonization improves their in vivo efficiency. For example, the dermal activity of rutin could be increased by a factor 1,000 comparing rutin nanocrystals with a water soluble derivative (WO2008/058755).

Antioxidants are also present in the peels of grapes (see Mattivi, F, Vrhovsek, U, Masuero, D, Trainotti, D, Differences in the amount and structure of extractable skin and seed tannins amongst red grape varieties; Australian Journal of Grape and Wine Research 2009; 15: 27-35; Bertelli, A A, Gozzini, A, Stradi, R, Stella, S, Bertelli, A; Stability of resveratrol over time and in the various stages of grape transformation. Drugs Exp Clin Res 1998; 24: 207-11). However, due to their poor solubility, these antioxidants cannot be exploited in products. The peels are therefore nowadays normally discarded. One aim of the present invention was therefore to formulate nanocrystals or amorphous nanoparticles of actives, e.g. from peels of grapes, as nanosized material, and to develop a process for the cost-effective production thereof.

Nanosized materials (having a size in the range of from 1 nm to 1,000 nm, referred to herein as the nanorange) have particular physico-chemical properties. These properties can be exploited for the improved delivery of poorly soluble actives in pharma (drugs, diagnostics), cosmetics (cosmetic actives) and nutrition (e.g. nutraceuticals) technology. Amongst these properties are increased saturation solubility, increased dissolution velocity, adhesiveness to surfaces/membranes in the body, and the small size itself allowing for example to use certain administration routes, e.g. intravenous injection. The particles can be crystalline (so called nanocrystals), or can be amorphous (so called amorphous nanoparticles), or can be a mixture of crystalline and amorphous (partially crystalline) particles. An overview about these nanosized materials is given in the reviews by C. M. Keck and R. H. Müller (Müller, R. H., C. M. Keck, Challenges and solutions for the delivery of biotech drugs—a review of drug nanocrystal technology and lipid nanoparticles. J Biotechnol, 2004. 113(1-3): p. 151-70.; Keck, C M, Müller, R H, Drug nanocrystals of poorly soluble drugs produced by high pressure homogenisation. Eur J Pharm Biopharm 2006; 62: 3-16.; Müller, R H, Gohla, S, Keck, C M, State of the art of nanocrystals—special features, production, nanotoxicology aspects and intracellular delivery. Eur J Pharm Biopharm 2011; 78: 1-9). The nanosized materials are typically produced in a liquid by wet milling. A suspension of nanosized material in a liquid is called nanosuspension.

Increased saturation solubility $C_s$ and increased dissolution velocity dc/dt enhance the oral bioavailability of poorly soluble drugs of class II of the biopharmaceutical classification system (BCS). Absorption of poorly soluble nutrients is also increased. Delivery of nanosized actives to the skin increases the penetration into the skin, yielding an increase in effect by up to a factor of 500 (Keck, C, Kobierski, S, Mauludin, R, Müller, R H, Second generation of drug nanocrystals for delivery of poorly soluble drugs: smartCrystals technology, Dosis 2, 126-130, 2008). Therefore these nanosized materials are of high commercial interest.

There are basically two approaches to create these nanosized materials, the "bottom-up" technologies and the "top-down" technologies. In the bottom-up technologies (e.g. precipitation), the nanosized material is obtained by precipitation. The active is dissolved in a solvent, the solvent is added to a non-solvent that is miscible with the solvent, and the particles precipitate. Depending on the precipitation conditions, either crystalline particles are obtained (e.g. so called "hydrosols" (GB Patent 2200048) or amorphous nanoparticles (e.g. product NanoMorph by the company Soliqs, Ludwigshafen, Knollstraße, Germany (U.S. Pat. No. 6,494,924 B1)). There are several disadvantages of the bottom-up technologies:

1. The use of organic solvents which need to be costly removed.
2. Potential solvent residues contaminating the product.
3. The process is costly, due to the use of large solvent quantities in case of very poorly soluble drugs.

For these reasons there are no or very few pharmaceutical products on the market that have been produced using bottom-up technologies.

Industrially feasible are the top-down technologies (e.g. bead milling, high pressure homogenization). Micrometer-sized material is reduced in size to the nanometer range by milling processes, in general wet milling. The major approaches are wet milling in bead/pearl mills (e.g. NanoCrystal product by the company élan, USA) or wet milling by high pressure homogenization. A review of these processes is given by R. H. Müller et al. (Müller, R H, Gohla, S, Keck, C M, State of the art of nanocrystals—special features, production, nanotoxicology aspects and intracellular delivery. Eur J Pharm Biopharm 2011; 78: 1-9).

Basically a certain total amount of energy input is required to reduce the size of the material to the nanorange. This total amount of energy can be generated by a low energy process over a long time, or a high energy process over a shorter time. Bead mill technology is low energy milling, whereas high pressure homogenization is high energy milling (pressures up to 1,500 or even up to 2,000 bar may be applied).

In the bead mill process, the material is suspended in a surfactant or stabilizer solution. The micrometer-sized suspension (i.e. macrosuspension) thus obtained is passed through a milling chamber containing fine milling beads (e.g. 1 mm in size or below). The milling beads are moved by an agitator, or by movement of the milling chamber itself. The material is ground to nanosize in between the moving milling beads, yielding a nanosuspension. The most pronounced disadvantages of a bead mill process are:
1. long milling times, up to hours and days (related to batch sizes of 1 kg to 100 kg);
2. potential product contamination due to the erosion of the milling beads during the long duration of the milling process; and
3. costs of the process due to the long processing times.

Therefore it would be desirable to have a process which is faster, minimizing production time and related costs.

During high pressure homogenization, the macrosuspension is milled by passing it through a homogenizer at high pressure. This may be a jet stream homogenizer (e.g. Microfluidizer by the company Microfluidics, Newton, Mass., USA (U.S. Pat. No. 6,337,092), or may be a piston gap homogenizer (e.g. APV Gaulin (Müller, R H, Becker R, Kruss B, Peters K, Pharmaceutical nanosuspensions for medicament administration as systems with increased saturation solubility and rate of dissolution, U.S. Pat. No. 5,858,410, WO96/14830, WO 01/03670).

The most pronounced disadvantages of high pressure homogenization are:
1. long production times because in many cases 20-50 passages (cycles) through the homogenizer are required; and
2. the high production pressure of up to 2,000 bar which can cause erosion from the machine (product contamination) or chemically decompose the processed active.

Therefore it is also desirable to be able to have shorter production times (reduced number of cycles) and to apply lower pressures.

The prior art describes attempts to obtain smaller sized nanocrystals or reducing the number of homogenization cycles by combining two production steps. Examples are the combination of spray drying and subsequent high pressure homogenization (DE 10 2005 011 786 A1, WO2006/094808) and freeze-drying and subsequent high pressure homogenization (DE 10 2005 017 777 A1, WO2006/108637). The disadvantages of these attempts are as follows:
1. The processes are relatively costly.
2. Spray drying, but especially lyophilisation, is time-consuming.
3. The number of cycles was reduced, but often still 5 (or even more) cycles are required.

Therefore, there is still a need for a more cost-efficient and faster production method. The present invention satisfies this need.

SUMMARY OF THE INVENTION

It has now surprisingly been found that the above objectives can be solved by a process for the preparation of nanocrystals or amorphous nanoparticles of actives.

The invention relates to a process for the production of nanocrystals or amorphous nanoparticles of actives (nanomaterials), especially from the peels of grapes. According to the process of the invention, a dispersion of a micrometer-sized material comprising an active in a solution of surfactant or a steric stabilizer is provided. The macro-suspension is then stirred for at least 1 minute at a rotational speed above 500 rpm using a rotor-stator mixer. The stirred mixture is passed through a jet stream or piston-gas type high pressure homogenizer to produce nanocrystals or amorphous nanoparticles of the active.

The process according to the invention is very economical and takes place under mild conditions. This excludes or minimizes any chemical decomposition. The nanomaterials according to the invention may be incorporated into formulations for use as nutraceutical, nutritional supplement, or as supportive treatment in medical therapy.

DESCRIPTION OF PREFERRED EMBODIMENTS OF THE INVENTION

Figure 1:
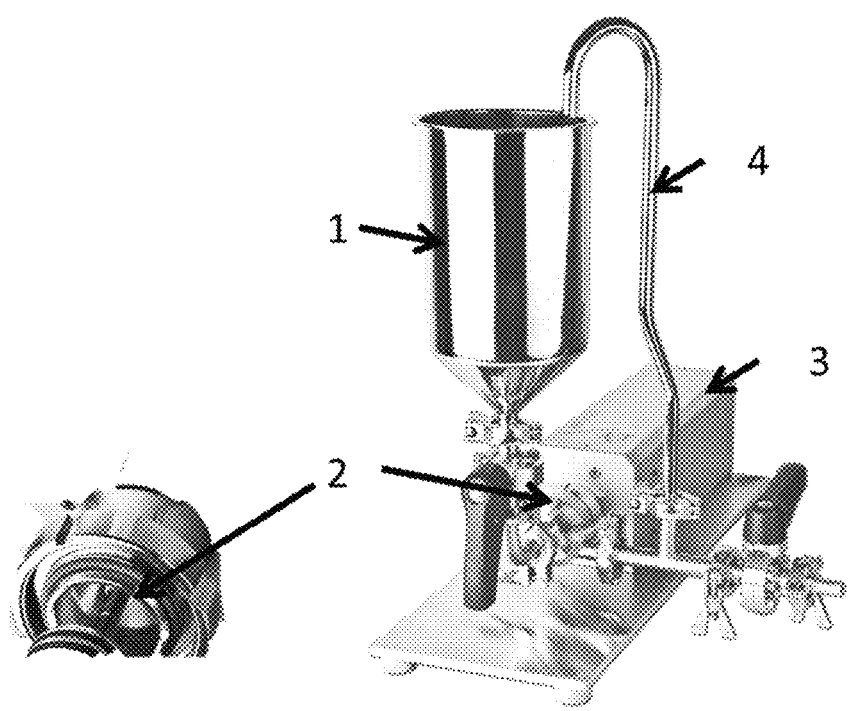
FIG. 1 illustrates a schematic drawing of an ART-MICCRA device with feeding container (1), rotor-stator unit (2), driving unit (3) and backflow tube to feeding container for circulation of suspension (modified figure, original photograph obtained from ART Prozess—& Labortechnik GmbH & Co. KG, Zienkener Str. 8a, Muellheim, Germany).

According to the process of the invention, a dispersion of a micrometer-sized material in a solution of surfactant or a steric stabilizer is provided. The macrosuspension is stirred for at least 1 minute at a rotational speed above 500 rpm, preferably above 5000 rpm, such as above 10,000 rpm, above 12,000 rpm, above 15,000 rpm, or even above 20,000 rpm, such as 20,000 to 40,000 rpm, in particular about 24000 rpm. This stirring can be effected using a rotor-stator mixer. The resultant mixture is then passed through a jet stream or piston-gas type high pressure homogenizer. The nanoparticles obtained in accordance with the invention have a mean PCS diameter in the nanometer range (1 nm-1,000 nm).

The rotor-stator mixer used in step ii) is preferably of the sprocket design type disclosed in U.S. Pat. No. 2,789,800 B1, the complete disclosure of which is incorporated herein by reference. In this rotor-stator mixer as used in accordance with the present invention, the gaps of the rotors are typically 1 mm or less wide, preferably 0.8 mm or less, in particular 0.6 mm or less, such as about 0.5 mm. The gap between rotor and stator is typically 0.5 mm or less wide, preferably 0.4 mm or less, such as 0.3 mm or less, and is in particular about 0.2 mm wide.

Nano peel grapes according to the invention can be either crystalline, amorphous, or partially crystalline and can be dispersed in water or aqueous solution as dispersion medium.

Surfactants that may be used in step i) are e.g. anionic (e.g. sodium lauryl sulphate), cationic (e.g. cetylpyridinium chloride), amphoteric (e.g. phospholipids), and non-ionic (e.g. polysorbates, especially Polysorbate 80 (=Tween 80)) surfactants. Possible polymeric stabilizers are e.g. macromolecules (e.g. albumin, gelatine, guar gum, xanthan, polysaccharides) or polymers (e.g. chitosan, poloxamers, polyvinyl alcohol, polyvinylpyrrolidine).

The actives processed are of a synthetic nature (e.g. cyclosporine), semi-synthetic (e.g. lipidic compounds such as coenzyme Q10) or purified actives extracted from plants (e.g. rutin), plant extracts or complete parts of plants (e.g. peels of grapes).

In an optional subsequent step iv), the dispersion medium may be removed, the nanoparticles being in a dry state and incorporated into oral dosage forms such as tablets, capsules, pellets or a powder for reconstitution to a suspension, or incorporated into dermal formulations. The peel grape formulation comprising the nanoparticles of the invention can be used as nutraceutical, nutritional supplement, or as supportive treatment in medical therapy, e.g. cancer treatment, being administered preferentially orally.

Devices for wet milling of nanosized materials need to have a certain minimum power density. The power density determines the resulting particle size. The higher the power density, the lower is the resulting particle size. When the minimum achievable particle size at a given power density is reached, further processing will not lead to further size reduction. Therefore with a high pressure homogenizer, application of a certain pressure will create the minimum particle size after typically 20 cycles. Additional cycles have been found to not diminute the crystals further.

Power densities in high pressure homogenizers are typically $10^{12}$ to $10^{13}$ Watt/m$^3$, leading to nanocrystals or amorphous nanoparticles. In contrast, high speed rotor-stator systems have a much lower power density, e.g. in the range $10^5$ to $10^7$ Watt/m$^3$ (Schuchmann, H P, Schuchmann H, Lebensmittelverfahrens-technik. 2005, Weinheim: Wiley VCH). Therefore, rotor-stator systems were not previously considered as suitable to produce nanosuspensions. They were only used to disperse the coarse micrometer-sized powder in the surfactant or stabilizer solution to from the macrosuspension which is then processed to a nanosuspension (Möschwitzer, J, Müller R H, Spray coated pellets as carrier system for mucoadhesive drug nanocrystals. Eur J Pharm Biopharm 2006; 62: 282-7; Mishra, P R, Al Shaal L, Müller R H, Keck C M, Production and characterization of Hesperetin nanosuspensions for dermal delivery. Int J Pharm 2009; 371: 182-9.) Rotor-stator systems that are generally used are those produced by the companies Janke & Kunkel (Janke und Kunkel-Str. 10, Staufen), IKA (Janke und Kunkel-Str. 10, Staufen) and Silverson Machines (German Office, Kolpingweg 12, Staufen).

It was not expected that, when processing a macrosuspension with a rotor-stator system, a nanosuspension would result. Especially, it was unexpected that this could be achieved even when processing hard materials such as rutin, for which 20 homogenization cycles at a high pressure of 1,500 bar are traditionally described to be required to obtain a size in the range of 700 nm (Mauludin, R, Müller R H, Keck C M, Kinetic solubility and dissolution velocity of rutin nanocrystals. Eur J Pharm Sci 2009; 36: 502-10; Mauludin, R, Müller R H, Keck C M, Development of an oral rutin nanocrystal formulation. Int J Pharm 2009; 370: 202-9). Especially surprising was that this could be achieved in a very short processing (production) time.

Nanonization can be achieved in accordance with the present invention by combining mixing in a rotor stator mixer, in particular one of the type ART MICCRA, developed recently by the company ART Prozess—& Labortechnik GmbH & Co. KG, Zienkener Str. 8a, Muellheim, Germany, with subsequent high pressure homogenization.

The process according to the invention can be characterized in that the total processing time is very short, only 2-4 minutes for dispersion of 1 kg suspension in the rotor stator mixer. A 1 kg batch can be processed in a homogenizer within just one minute (APV LAB 60, APV Deutschland GmbH, Zechenstrasse 49, Unna, Germany) or less. The subsequent step at high pressure is characterized that in contrast to traditional homogenization for the production of nanocrystals:
1. only 8 cycles or less than 5 cycles are applied, typically only 1-2 cycles, and
2. that preferentially pressures that are not excessively high can be used, e.g. 1,500-2,000 bar are applied, more preferred low pressures, i.e. below 1,500 bar or 1,001 bar, below 501 bar, and especially at 300 bar or below.

Figure 2:
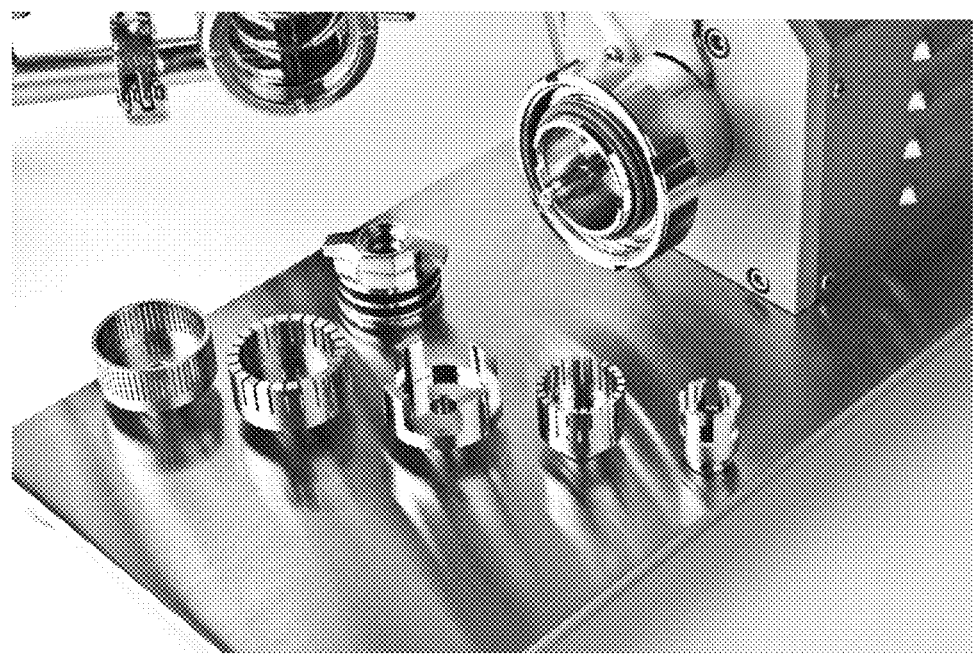
FIG. 2 illustrates a picture of sprockets mounted in the rotor-stator unit (photograph obtained from ART Prozess—& Labortechnik GmbH & Co. KG, Zienkener Str. 8a, Muellheim, Germany).

The ART-MICCRA® rotor stator as preferably employed according to the present invention is characterized in that the suspension is fed from a feeding container via a tube to the rotor-stator unit, which is driven by a driving unit (see FIG. 1). An important part is the design of the rotor-stator unit, which is depicted in FIG. 2. The claimed rotor-stator system in this invention is based on the depicted design of the sprockets, its dimensions and surface forms. The process using the rotor-stator ART-MICCRO can take place batch-wise in a discontinuous mode (e.g. Example 1, 1 kg batch), or in a flow-through chamber with built-in ART-MICCRO stirrer, allowing a larger scale.

Example 1 shows that the rotor-stator is, by itself, not able to produce a nanosuspension. The diameter 50% is around 1.5 µm, which would be expected. Subsequent processing by high pressure homogenization (i.e. in accordance with the present invention) applying 8 cycles of low pressures (250 bar to 1,000 bar) yielded a diameter as small as 439 nm (Example 2). This is surprising because processing a rutin macrosuspension by pre-dispersion with an Ultra Turrax and traditional high pressure homogenization yielded, after 20 cycles at 1,500 bar, a PCS diameter of 727 nm (Mauludin, R, Müller R H, Keck C M, Development of an oral rutin nanocrystal formulation. Int J Pharm 2009; 370: 202-9). Obviously, the mixing with the ART-MICCRA rotor stator makes the material more susceptible to diminution, even at lower pressures (power densities).

The low pressures applied in Example 2 are comparable to the so called "pre-milling" in the traditional high pressure homogenization. In this pre-milling cycles of increasing pressure are applied to avoid blockage of the homogenization gap by large particles present in the macrosuspension. Typically, one would apply e.g. 2 cycles at 300 bar, 2 cycles at 500 bar, 1 cycle at 1,000 bar (Kobierski, S, Ofori-Kwakye K, Müller R H, Keck C M, Resveratrol nanosuspensions for dermal application—production, characterization, and physical stability. Pharmazie 2009; 64: 741-7). In this pre-milling, the obtained laser diffraction median diameter 50% was 7.44 µm. In contrast, the median diameter 50% in accordance with the invention (Example 2) is only 0.36 µm. This demonstrates that the rotor-stator stirring by the ART-MICCRO makes the materials more susceptible to diminution.

In accordance with Example 3, the suspension was homogenized by applying an additional 20 homogenization cycles, typically applied in the traditional high pressure homogenization. This should allow a comparison of the process efficiency. The traditional high pressure homogenization yielded, after 20 cycles, laser diffractometry diameters 50% of 0.840 µm, and 90% diameters of 1.845 µm (Mauludin, R, Müller, R H, Keck, C M, Kinetic solubility and dissolution velocity of rutin nanocrystals. Eur J Pharm Sci 2009; 36: 502-10). The laser diffraction diameters of the invention process were diameter 50% 0.33 µm, diameter 90% 0.72 µm.

The conclusions that can be drawn from the above are therefore as follows:
1. The process according to the invention yields after identical cycle numbers and pressures diameters 50% of almost just one third, as compared to traditional high pressure homogenization.
2. This small size is obtained already after the low pressure cycles (0.36 µm) without running the additional 20 cycles leading to 0.33 µm, demonstrating the efficiency of the inventive process: Much smaller sizes in distinctly less cycle numbers at lower pressures.

Example 4 shows the result when using Plantacare as surfactant, yielding a median diameter 50% of 0.38 µm. In Example 5, one additional homogenization cycle at 300 bar is applied, which does not reduce the median size (bulk) but clearly removed some remaining aggregates as indicated by the decrease in the diameter 90% from 29.3 µm in Example 4 to just 0.88 µm in Example 5.

The process of the invention is also superior to bead milling. To obtain the smallest achievable median diameter 50% for a rutin nanosuspension 3-4 passages through the bead mill were required, after 10 passages the diameter 50% was still 0.73 µm (Kobierski, S, Hanisch, J, Mauludin, R, Müller, R H, Keck, C, Nanocrystal production by smartCrystal combination technology, Int. Symp Control Rel Bioact Mater 35, #3239, New York City, 2008).

EXAMPLES

Example 1

Rutin powder was dispersed in water and analyzed by laser diffractometry (Coulter LS 230, Beckman-Coulter, USA) applying the Mie theory (real refractive index 1.59, imaginary index 0.01). The volume median diameter 50% was 10.64 µm, the diameter 90% was 118.57 µm and the diameter 99% 195.23 µm, respectively. This rutin powder was dispersed in water and Tween 80, yielding a composition of 18% rutin, 2.0 Tween 80 and 80.0% water (=macrosuspension), total weight 1.0 kg.

The suspension was cooled to about 10° C., then dispersion was performed using an ART-MICCRA rotor stator for 4 minutes, 24,000 rounds per minute (RPM), keeping the temperature below 30° C. Particle size was analyzed by laser diffractometry (Mastersizer 2000, Malvern Instr., United Kingdom), applying Mie theory (real refractive index 1.53, imaginary index 0.01). The diameter 50% was 1.5 µm.

Example 2

11.11 g of the suspension from Example 1 was mixed with 28.89 g of Tween 80 solution. This resulted in a final composition of 5.0% rutin, 2.0=% Tween 80, 93.0% water. This suspension was homogenized for 2 cycles at 250 bar, 2 cycles at 500 bar, 2 cycles at 750 bar, and 2 cycles at 1000 bar. This resulted in a particle size of 439 nm and a polydispersity index of 0.893 (measured by photon correlation spectroscopy (PCS), measured in saturated rutin solution, Malvern Zetasizer Nano ZS, Malvern Instr., United Kingdom). The analysis by the Mastersizer yielded a diameter 50% of 0.36 µm and a diameter 90% of 0.98 µm.

Example 3

The suspension of Example 2 was homogenized for an additional 20 cycles at 1,500 bar, yielding a PCS diameter of 381 nm and a polydispersity index of 0.807. Mastersizer diameters were diameter 50% 0.33 µm, 90% 0.72 µm.

Example 4

11.111 g of the suspension from Example 1 were admixed by stirring with a mixture of 28.489 g of distilled water and 0.400 g of Plantacare 2000. This resulted in the final composition of 5.0% rutin, 0.56% Tween 80, 1.0% Plantacare 2000, and 93.44% water. This suspension was homogenized for 1 cycle at a low pressure of 300 bar (Micron LAB40, APV Homogenizer GmbH, Unna, Germany).

The PCS diameter was 606 nm, the polydispersity index 0.215 (Malvern Zetasizer Nano ZS), being in agreement to the laser diffraction diameter 50% of 0.38 µm (Mastersizer 2000, Mie theory).

Example 5

The suspension of Example 4 was homogenized applying 1 further cycle at 300 bar (i.e. a total of 2 cycles at 300 bar applied to the suspension). The PCS diameter was 610 nm, the polydispersity index 0.170 (Malvern Zetasizer Nano ZS), being well in agreement to the laser diffraction diameter 50% of 0.31 µm (Mastersizer 2000, Mie theory). The diameter 90% decreased to 0.88 µm, from 29.3 µm in Example 4, indicating reduction of few remaining aggregates and increased homogeneity of the size distribution.

While the claimed invention has been described in detail and with reference to specific embodiments thereof, it will be apparent to one of ordinary skill in the art that various changes and modifications can be made to the claimed invention without departing from the spirit and scope thereof.

The invention claimed is:

1. A process for the preparation of nanocrystals or amorphous nanoparticles of an active comprising:
   i) providing a macrosuspension comprising a dispersion of a micrometer-sized material comprising an active in a solution of a surfactant or a steric stabiliser, wherein the active is in the solid state and remains in the solid state during the process;
   ii) stirring the macrosuspension for at least 1 minute at a rotational speed above 500 rounds per minute (rpm) using a rotor-stator mixer; and
   iii) passing the macrosuspension through a jet stream or piston-gap type high pressure homogenizer to produce nanocrystals or amorphous nanoparticles of the active wherein the homogenization in step iii) takes place at a pressure below 1,500 bar applying up to 20 homogenization cycles maximum.

2. The process according to claim 1, wherein the rotational speed in step ii) is above 5000 rpm.

3. The process according to claim 1, wherein the rotational speed in step ii) is above 10,000 rpm 4. The process according to claim 1, wherein the rotational speed in step ii) is above 12,000 rpm 5. The process according to claim 1, wherein the rotational speed in step ii) is above 15,000 rpm.

6. The process according to claim 1, wherein the rotational speed in step ii) is above 20,000 rpm.

7. The process according to claim 1, wherein the rotational speed in step ii) is 20,000 to 40,000 rpm 8. The process according to claim 1, wherein the rotational speed in step ii) is about 24,000 rpm.

9. The process according to claim 1, wherein the gaps of the rotor of the rotor-stator mixer as used in step ii) are 1 mm or less wide.

10. The process according to claim 1, wherein the gaps of the rotor of the rotor-stator mixer as used in step ii) are 0.8 mm or less.

11. The process according to claim 1, wherein the gaps of the rotor of the rotor-stator mixer as used in step ii) are 0.6 mm or less.

12. The process according to claim 1, wherein the gaps of the rotor of the rotor-stator mixer as used in step ii) are about 0.5 mm.

13. The process according to claim 1, wherein the gap between rotor and stator in the rotor-stator mixer used in step ii) is 0.5 mm or less wide.

14. The process according to claim 1, wherein the gap between rotor and stator in the rotor-stator mixer used in step ii) is 0.4 mm or less wide.

15. The process according to claim 1, wherein the gap between rotor and stator in the rotor-stator mixer used in step ii) is 0.3 mm or less wide.

16. The process according to claim 1, wherein the gap between rotor and stator in the rotor-stator mixer used in step ii) is about 0.2 mm wide.

17. The process according to claim 1, wherein step ii) is effected batch-wise in a discontinuous mode or in a flow-through chamber.

18. The process according to claim 1, wherein the homogenization in step iii) takes place at a pressure below 1,001 bar applying up to 8 homogenization cycles maximum.

19. The process according to claim 1, wherein the homogenization in step iii) takes place at a pressure below 501 bar applying up to 5 homogenization cycles maximum.

20. The process according to claim 1, wherein the homogenization in step iii) takes place at a pressure at 300 bar or below 300 bar applying 1-2 homogenization cycles maximum.

21. The process according to claim 1, wherein the active is derived from peels of grapes.

22. A process for the preparation of nanocrystals or amorphous nanoparticles of an active comprising:
  i) providing a macrosuspension comprising a dispersion of a micrometer-sized material comprising an active in a solution of a surfactant or a steric stabiliser, wherein the active is in the solid state and remains in the solid state during the process;
  ii) stirring the macrosuspension for at least 1 minute at a rotational speed above 500 rounds per minute (rpm) using an ART-MICCRA-type rotor-stator mixer; and
  iii) passing the macrosuspension through a jet stream or piston-gap type high pressure homogenizer to produce nanocrystals or amorphous nanoparticles of the active.

* * * * *